US010653625B2

(12) United States Patent
Rosenberg et al.

(10) Patent No.: US 10,653,625 B2
(45) Date of Patent: May 19, 2020

(54) PRODUCTION OF DOSAGE FORMS COMPRISING A SOLID DISPERSION OF A MICROCRYSTALLINE AGENT

(75) Inventors: Jörg Rosenberg, Ellerstadt (DE); Markus Mägerlein, Mannheim (DE); Bernd Liepold, Heidelberg (DE); Jörg Breitenbach, Mannheim (DE)

(73) Assignee: Abbvie Deutschland GmbH & Co. KG, Wiesbaden (DE)

( * ) Notice: Subject to any disclaimer, the term of this patent is extended or adjusted under 35 U.S.C. 154(b) by 1335 days.

(21) Appl. No.: 11/884,164

(22) PCT Filed: Feb. 9, 2006

(86) PCT No.: PCT/EP2006/001164
§ 371 (c)(1),
(2), (4) Date: May 1, 2008

(87) PCT Pub. No.: WO2006/084696
PCT Pub. Date: Aug. 17, 2006

(65) Prior Publication Data
US 2009/0012184 A1 Jan. 8, 2009

(30) Foreign Application Priority Data

Feb. 11, 2005 (EP) .................... 05002955

(51) Int. Cl.
*A61K 47/30* (2006.01)
*A61K 9/14* (2006.01)
(52) U.S. Cl.
CPC .............. *A61K 9/146* (2013.01); *A61K 9/145* (2013.01)
(58) Field of Classification Search
None
See application file for complete search history.

(56) References Cited

U.S. PATENT DOCUMENTS 6,132,772 A * 10/2000 Sherman ............. A61K 9/146
424/461
6,224,793 B1 * 5/2001 Hoffman et al. ............ 264/4.1
2003/0031705 A1 * 2/2003 Sherman ..................... 424/452
2003/0170309 A1   9/2003 Babcock et al.
2006/0024370 A1 * 2/2006 Nguyen et al. ............. 424/484

FOREIGN PATENT DOCUMENTS

| DE | 3520184      | 12/1985 |
| EP | 0 156 080 A1 | 10/1985 |
| GB | 2 160 100 A  | 12/1985 |
| WO | 93/20138 A2  | 10/1993 |
| WO | WO 99/21534  | * 5/1999 |

OTHER PUBLICATIONS

Chiou (Journal of Pharmaceutical Sciences, 60(9), 1281-1302, 1971) Pharmaceutical applications of solid disperion systems.*
Verreck (European Journal of Pharmaceutical Sciences, 26, 349-358, 2005), The effect of pressurized . . . .*
Rasenack et al. (International Journal of Pharmaceutics, 254, 137-145, 2003) Microcrystals for dissolution.*
PCT/IB/373, PCT/ISA/237, Sep. 20, 2007.
PCT/IB/338, Sep. 20, 2007.
Accelerators: Kollidon® CL, Kollidon® CL-F, Kollidon® CL-SF, Kollidon® CL-M Super-Disintegrants and Dissolution Enhancers—BASF Jan. 2009.
Technical Information: Kollidon® VA 64, Kollidon® VA 64 Fine—BASF Pharma Ingredients & Services Aug. 2011.

* cited by examiner

*Primary Examiner* — Tigabu Kassa
(74) *Attorney, Agent, or Firm* — Saul Ewing Arnstein & Lehr LLP; Brian R. Landry; Justin W. Crotty

(57) ABSTRACT

A method is described for the production of dosage forms, which comprise a solid dispersion of a microcrystalline active substance, in which a thermoplastic polymer with a glass transition temperature Tg of at least 40° C. is melted and an active substance is dissolved homogeneously in the melt; crystallization of the active substance is initiated in the mass obtained; and the mass is cooled. Crystallization of the active substance can be initiated by adding a nonsolvent, seed crystals of the active substance or a derivatization reagent. In addition, crystallization can be initiated by holding the mass for a sufficient length of time at a temperature that is below the temperature at which the active substance is completely soluble in the mass.

13 Claims, 1 Drawing Sheet

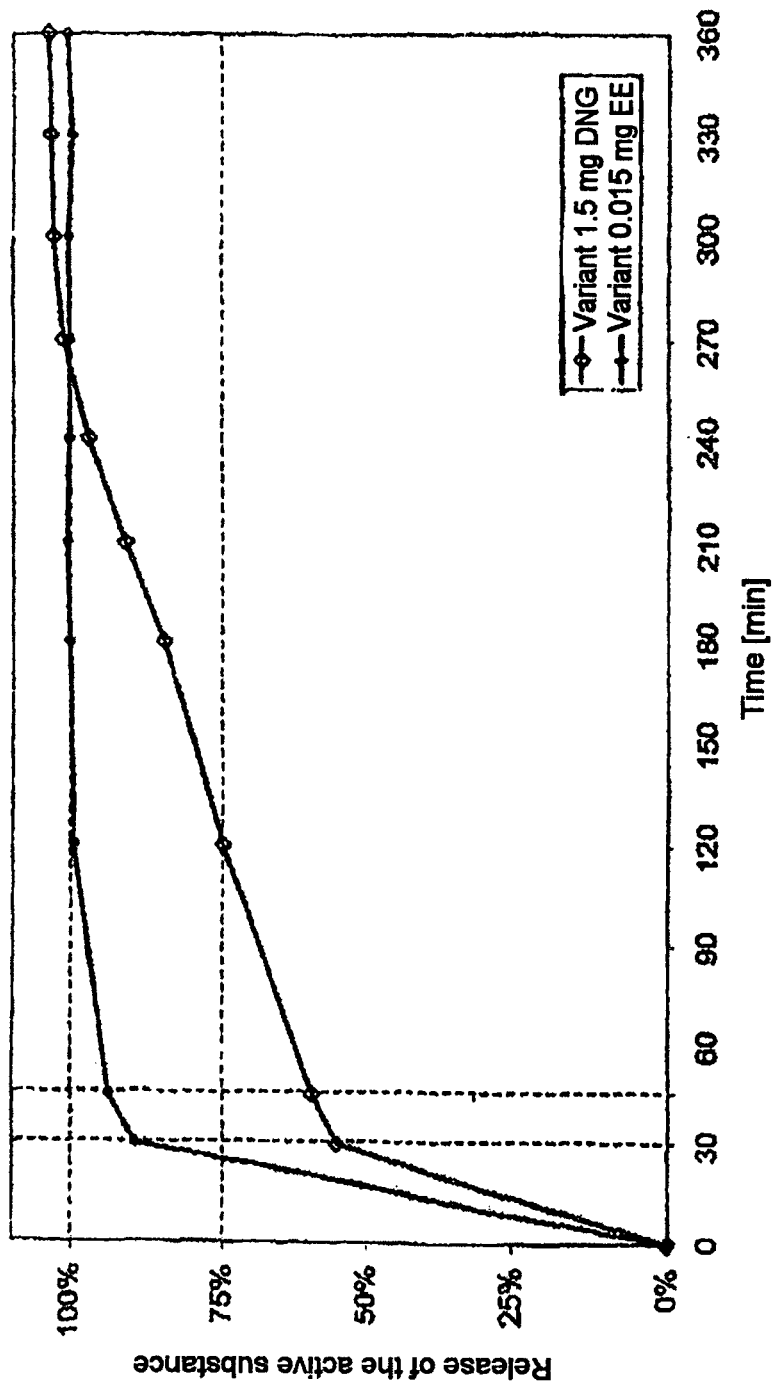

PRODUCTION OF DOSAGE FORMS COMPRISING A SOLID DISPERSION OF A MICROCRYSTALLINE AGENT

This application is the U.S. national phase application, pursuant to 35 U.S.C. § 371, of PCT international application Ser. No. PCT/EP2006/001164, filed Feb. 9, 2006, designating the United States and published in German on Aug. 17, 2006 as publication WO 2006/084696 A1, which claims priority to European Patent Application Ser. No. 05 002 955.2, filed Feb. 11, 2005. The entire contents of the aforementioned patent applications are incorporated herein by this reference.

The present invention relates to a method of production of dosage forms that comprise a solid dispersion of a microcrystalline active substance.

In order to improve the bioavailability of sparingly-soluble active substances, it is desirable to increase the surface area of the active substances, i.e. comminute the active substances to very small particles. However, the known grinding technologies have various disadvantages. Very long grinding times are required to obtain sufficiently small particles. Abrasive wear of the grinding media used and contamination of the active substance with residues from the mill are often unavoidable.

The production of small crystals of active substance by controlled crystallization of the active substance is known. EP-A 0 156 080 describes the production of a preparation of active substance for transdermal use. An active substance and a polymer are dissolved in a solvent; the solution is spread on a carrier. On drying, a proportion of the active substance crystallizes in the form of small particles.

DE 35 20 184 discloses a prolonged-release galenic form in which an active substance in continuous crystalline form is contained in a water-soluble crystalline matrix. For production, the active substance is dissolved in molten polyethylene glycol and the melt is then cooled. Polyethylene glycols typically have glass transition temperatures of less than 0° C. Owing to the low glass transition temperature, the galenic forms display a low softening temperature; the galenic forms therefore tend to display cold flow and have inadequate storage stability. Furthermore, many active substances do not have sufficient solubility in molten polyethylene glycol. Polyethylene glycols belong to the ether class of substances. These are known to have a tendency to form peroxides, especially under the influence of light, heat and oxygen. Polyethylene glycols are therefore incompatible with oxidation-sensitive active substances such as antibiotics.

WO 93/20138 describes a two-stage process for incorporating a partially soluble compound in a polymer matrix. A first portion of the compound is mixed in soluble phase with the polymer near the saturation concentration; then a second portion of the compound is mixed into the polymer, so that it does not dissolve in the polymer. Deposition of the dissolved portion on the particles of the second portion is said to be avoided.

It has now been found that crystals of active substance of suitable size can be crystallized in a controlled manner from certain polymer melts. The crystals of active substance are at the same time embedded in a polymer matrix and stabilized.

The invention therefore relates to a method of production of dosage forms with a solid dispersion of a microcrystalline active substance, in which
 a) an active substance is dissolved homogeneously in the melt of a thermoplastic polymer with a glass transition temperature Tg of at least 40° C., preferably at least 40 to 160° C., in particular 50 to 120° C.;
 b) crystallization of the active substance is initiated in the mass obtained;
 c) the mass is cooled.

For example, crystallization of the active substance is initiated at a temperature at or above the Tg of the polymer in step b), and the mass is then cooled in step c) to a temperature below the Tg.

The microcrystals of active substance are embedded, in the solid dispersion obtained, in a matrix of the thermoplastic polymer and are accordingly stabilized against agglomeration and similar phenomena. The presence and close spatial proximity of the polymer and optionally of solubilizers facilitate the solubilization of the active substance during application of the dosage form. There is consequently an overall improvement in the bioavailability of the active substance.

The microcrystals typically have an average particle size (in the direction of the largest spatial extent) from 500 nm to 100 µm, preferably from 1 µm to 80 µm and in particular from 5 µm to 50 µm.

FIG. 1 is a graph showing the precent relief of the active substance over time for the varient 1.5 mg ONG as compared to the varient 0.015 mg EE.

"Dosage forms" are to be understood as all forms that are suitable for use as medicinal products, in particular for oral administration, plant treatment agents, animal feeds and dietary supplements. These include for example tablets of any form, pellets or granules. They further include forms such as sheets, films, implants and suppositories.

"Melt" means a pourable mixture that is capable of undergoing a transition to a solid state on lowering the temperature, owing to a phase transition of the thermoplastic polymer contained therein.

The "glass transition temperature" (abbreviated to "Tg" hereinafter) is an important parameter for characterizing the physical properties of a thermoplastic polymer. When a liquefied polymer is cooled, the polymer "freezes" to a grasslike state. Transition to the glasslike state without crystallization is termed "glass transition". The temperature of this transition is the "Tg". The transition is essentially a "freezing-in", i.e. a relaxation process. At or below the Tg there is no longer any segmental mobility; there is no micro-Brownian movement. The Tg can be influenced by adding plasticizers. Generally the Tg decreases with increasing plasticizer content. For the purposes of the present application, the glass transition temperature is to be understood as that which the polymer displays in the mass, i.e. taking into account any plasticizers present and any plasticizing effects of other components.

For production of the solid dosage forms, a melt, i.e. a pourable cohesive mass, in which the active substance is dissolved, is prepared at an elevated temperature, i.e. a temperature at or above the softening point of the thermoplastic polymer, e.g. in the range from 80 to 200° C., preferably 90 to 180° C. Crystallization of the active substance is initiated in the mass.

Crystallization can be initiated in the melt, i.e. in the still pourable mass, or in the mass that is no longer pourable but not yet completely solidified. The mass is then cooled and solidified, optionally after a forming step.

It is preferable for crystallization to be initiated at a temperature of at least 35° C., in particular at least 45° C. In certain embodiments, crystallization is initiated at or above the Tg of the polymer. In this way, small particles of largely uniform particle size are obtained reproducibly. The method according to the invention therefore differs from the phenomenon of (unwanted) recrystallization of active substances from molecular-dispersion preparations, which are also termed solid solutions, during storage. In these uncontrolled recrystallization phenomena, particles form with very heterogeneous size distribution.

Crystallization can be initiated in various ways, which are described in detail below. Two or more of the measures described can of course be combined.

In one embodiment of the method according to the invention, a nonsolvent is added to the mass, thus initiating crystallization of the active substance. "Nonsolvent" means a compound in which the active substance is insoluble or sparingly soluble (e.g. less than 1 g active substance in 100 ml nonsolvent at the temperature of addition) and that is preferably completely miscible with or soluble in the other components of the mass. The nonsolvent is as a rule a liquid or a melt and is preferably selected such that it is physiologically compatible. The nonsolvent can be a low-molecular compound, such as water, alcohols such as ethanol, n-propanol, isopropanol or n-butanol, polyols such as ethylene glycol, propylene glycol, diethylene glycol or glycerol, polyalkylene glycols such as polyethylene glycols (preferably with a number-average molecular weight of less than 1000), lipids such as triglycerides. Advantageously, the nonsolvent is mixed homogeneously with the melt, preferably in shearing conditions.

In a second embodiment of the method according to the invention, seed crystals of the active substance are added to the mass, thus initiating crystallization of the active substance. The temperature of the mass when the seed crystals are added is advantageously selected such that no notable dissolving of the seed crystals occurs, i.e. at the temperature that is selected, the mass should essentially be saturated or supersaturated with respect to the active substance. The seed crystals are preferably added as a suspension in a suitable suspending medium.

In a third embodiment, by adding a derivatization reagent, the active substance is converted to a difficulty soluble derivative of the active substance, which crystallizes out. If the active substance has acid or basic groups, by adding bases or acids it can be converted to a salt of basic or acid addition, which may have lower solubility in the mass than the free active substance. Suitable bases or acids are selected from the usual physiologically compatible bases and acids. Suitable bases are e.g. sodium or potassium carbonate, sodium or potassium hydrogen carbonate, amine bases, such as triethanolamine or lysine and the like. As physiologically compatible organic and inorganic acids, the following may be considered, for example: hydrochloric acid, hydrobromic acid, phosphoric acid, sulphuric acid, $C_1$-$C_4$-alkylsulphonic acids such as methanesulphonic acid, aromatic sulphonic acids such as benzenesulphonic acid and toluenesulphonic acid, acetic acid, citric acid, malic acid, succinic acid, aspartic acid, glutamic acid, crotonic acid, glycolic acid, acetylsalicylic acid, oxalic acid, maleic acid, fumaric acid, lactic acid, tartaric acid, adipic acid and benzoic acid.

Other derivatization reagents that may be considered are complexing agents such as cyclodextrins.

The derivatization reagent is preferably added in liquid or dissolved form to the mass.

In a fourth embodiment of the method according to the invention, crystallization of the active substance is initiated by holding the melt for a sufficient length of time at a temperature that is below the temperature at which the active substance is completely soluble in the melt and which is preferably at least 35° C., in particular at least 45° C. This embodiment makes use of the temperature-dependent solubility of the active substance in the mass. On controlled cooling of the mass, the active substance crystallizes out of the mass.

Crystallization of the active substance can be accompanied by transformation of a polymorphic form of the active substance used initially, to another polymorphic form of the active substance.

Thermoplastic polymers that can be considered for the method according to the invention include physiologically compatible, water-soluble or water-dispersible polymers with a Tg of at least 40° C., preferably 50 to 180° C., which can be melted without decomposition, or without notable decomposition. Polymers that can be melted on adding suitable plasticizers are also suitable.

Suitable thermoplastic polymers are for example
polyvinylpyrrolidone (PVP),
copolymers of n-vinyl pyrrolidone and vinyl acetate and/or vinyl propionate,
copolymers of vinyl acetate and crotonic acid,
partially saponified polyvinyl acetate, polyvinyl alcohol,
polyhydroxyalkyl acrylates, polyhydroxyalkyl methacrylates,
polyacrylates and polymethacrylates (Eudragit types),
copolymers of methylmethacrylate and acrylic acid,
polyethylene glycols,
alkylcelluloses, in particular methylcellulose and ethylcellulose,
hydroxyalkylcelluloses, in particular hydroxypropylcellulose (HPC),
hydroxyalkyl-alkylcelluloses, in particular hydroxypropylmethylcellulose (HPMC),
cellulose esters such as cellulose phthalates, in particular cellulose acetate-phthalate,
hydroxypropylmethylcellulose phthalate and hydroxypropylmethylcellulose acetate-succinate (HPMCAS).

Of these, homo- or copolymers of vinyl pyrrolidone are especially preferred, e.g. poly-vinylpyrrolidone with K-values according to Fikentscher from 12 to 100, preferably 17 to 30, or copolymers of 30 to 70 wt. % n-vinyl pyrrolidone (VP) and 70 to 30 wt. % vinyl acetate (VA), such as a copolymer of 60 wt. % VP and 40 wt. % VA. Hydroxypropylcellulose and hydroxypropylmethylcellulose are also especially preferred.

Mixtures of said polymers can of course also be used. The solubility of the active substance in the melt should preferably be more than 20 wt. %, in particular more than 40 wt. %, relative to the sum of active substance, polymer and optional components.

"Active substances" in the sense of the invention means all substances with a desirable physiological effect on the human or animal body or on plants. This includes in particular pharmaceutical active substances. The amount of active substance per unit dose can vary widely. As a rule it is selected such that it is sufficient to achieve the desired effect. Combinations of active substances can also be used.

The active substance is preferably insoluble or difficulty soluble in water (less than 5 g active substance, in particular less than 1 g active substance, dissolves in 100 ml water at 22° C.).

Examples of said insoluble or difficulty soluble compounds are
Analgesics and anti-inflammatories such as fentanyl, indomethacin, ketoprofen, nabumetone, oxyphenbutazone, paracetamol, phenylbutazone, piroxicam, tramadol; antiarrhythmics, such as gallopamil, procainamide, quinidine, verapamil;

Anti-infectives such as amoxicillin, ampicillin, benzathine, penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxycycline, erythromycin, flucloxacillin, halofantrine, isoniazid, kanamycin, lincomycin, mefloquine, minocycline, nafcillin, neomycin, norfloxacin, ofloxacin, oxacillin, phenoxymethyl-penicillin, pyrimethamine-sulphadoxine, quinine, streptomycin; anticoagulants such as warfarin;

Antidepressants such as amitriptyline, amoxapine, atibeprone, butriptyline, clomipramine, desipramine, dothiepin, doxepin, fluoxetine, fluvoxamine, gepirone, imipramine, mianserin, milnacipran, nortriptyline, paroxetine, sertraline;

Antidiabetics such as glibenclamide, metformin;

Antiepileptics such as carbamazepine, clonazepam, ethosuximide, phenobarbitone, phenyloin, primidone, topiramate, valpromide;

Antimycotics such as amphotericin, clotrimazole, econazole, fluconazole, flucytosine, griseofulvin, itraconazole, ketoconazole, miconazole nitrate, nystatin, terbinafine, voriconazole;

Antipodagric agents such as benzbromarone, probenecid;

Antihistamines such as astemizole, cinnarizine, cyproheptadine, descarboethoxyloratadine, fexofenadine, flunarizine, levocabastine, loratadine, norastemizole, oxatomide, promethazine, terfenadine;

Antihypertensives such as captopril, clonidine, cyclizine, diazoxide, dihydralazine, enalapril, fosinopril, guanethidine, ketanserin, lisinopril, minoxidil, prazosin, ramipril, rescinnamine, reserpine, terazosin;

Muscarinic antagonists such as atropine sulphate, hyoscine;

Virostatics such as acyclovir, AZT, ddC, ddI, ganciclovir, loviride, tivirapine, 3TC, delavirdine, indinavir, nelfinavir, ritonavir, saquinavir, lopinavir;

Cytostatics and antimetabolites such as Adriamycin, cladribine, dactinomycin, daunorubicin, doxorubicin, etoposide, mitomycin, mitoxantrone, paclitaxel, Taxol, Taxotere, trimetrexate, vincristine, vinblastine;

Antimigraine agents such as alniditan, naratriptan, sumatriptan;

Antiparkinsonian agents such as bromocriptine mesylate, carbidopa, levodopa, selegiline;

Antipsychotics, hypnotics, anxiolytics and sedatives such as alprazolam, buspirone, chlordiazepoxide, chiorpromazine, chlorprothixene, clozapine, diazepam, flupentixol, fluphenazine, flurazepam, haloperidol, 9-hydroxyrisperidone, lorazepam, mazapertine, melperone, methaqualone, olanzapine, oxazepam, pimozide, pipamperone, piracetam, promazine, risperidone, selfotel, Seroquel, sertindole, sulpiride, temazepam, thioridazine, thiothixene, triazolam, trifluoperazine, trifluperidol, triflupromazine, ziprasidone, zolpidem;

Neuroprotective agents such as lubeluzole, lubeluzole oxide, riluzole, aptiganel, eliprodil, remacemide;

Antitussives such as dextromethorphan, laevodropropizine, noscapine;

Beta-blockers such as atenolol, bupranolol, carvedilol, labetalol, metipranolol, metoprolol, nebivolol, oxprenolol, propanolol;

Inotropics such as aminone, digitoxin, digoxin, milrinone;

Corticosteroids such as beclomethasone-dipropionate, betamethasone, budesonide, cortisone, dexamethasone, fludrocortisone, hydrocortisone, methylprednisolone, paramethasone, prednisolone, prednisone, triamcinolone;

Antiseptics such as chlorhexidine;

Diuretics such as acetazolamide, amiloride, benzthiazide, chlorothiazide, chlorthalidone, dichlorphenamide, ethacrynic acid, ethoxzolamide, frusemide, hydrochlorothiazide, hydroflumethiazide, isosorbide, polythiazide, spironolactone, triamterene, trichlormethiazide;

Ergot alkaloids such as co-dergocrine, ergotamine, nicergoline;

Gastrointestinal agents such as bromopride, cimetidine, cisapride, clebopride, diphenoxylate, domperidone, famotidine, lansoprazole, loperamide, loperamide oxide, mesalazine, metoclopramide, Mosapride, nizatidine, norcisapride, olsalazine, omeprazole, pantoprazole, perprazole, pirenzepine, prucalopride, ranitidine, rabeprazole, ridogrel, sulphasalazine;

Haemostatics such as aminocapronic acid;

Immunosuppressants such as cyclosporin A, tacrolimus;

Antilipaemics such as atorvastatin, lovastatin, pravastatin, probucol, simvastatin, fenofibrinic acid, fenofibrate;

Local anaesthetics such as benzocaine, lignocaine;

Opioid analgesics such as buprenorphine, codeine, dextromoramide, dextropropoxyphene, dihydrocodeine, hydrocodone, oxycodone, morphine, papaverine, pentazocine, pethidine;

Parasympathomimetics such as eptastigmine, galanthamine, metrifonate, neostigmine, physostigmine, tacrine, donepezil, rivastigmine, milameline, sabcomeline, talsaclidine, Xanomeline, memantine, lazabemide;

Hormones, e.g. androgens such as methyltestosterone, oxymetholone, stanozolol; oestrogens such as conjugated oestrogens, ethinylestradiol, mestranol, oestradiol, oestriol, oestrone; progestogens; chlormadinone acetate, cyproterone acetate, 17-deacetylnorgestimate, desogestrel, dienogest, dydrogesterone, ethynodiol diacetate, gestodene, 3-ketodesogestrel, levonorgestrel, lynestrenol, medroxyprogesterone acetate, megestrol, norethindrone, norethindrone acetate, norethisterone, norethisterone acetate, norethynodrel, norgestimate, norgestrel, norgestrienone, progesterone, quingestanol acetate;

Stimulants such as sildenafil;

Sympathomimetics such as ephedrine, clenbuterol, fenoterol, norfenefrine, pseudoephedrine;

Vasodilators such as amlodipine, buflomedil, buphenine, carbocromen, diltiazem, dipyridamole, isosorbide dinitrate, lidoflazine, molsidomine, nicardipine, nifedipine, nimodipine, oxpentifylline.

The mass can in addition comprise various optional excipients. These optional excipients are:

Plasticizers such as $C_7$-$C_{30}$-alkanols, ethylene glycol, propylene glycol, glycerol, trimethylolpropane, triethylene glycol, butanediols, pentanols, such as pentaerythritol and hexanols, polyalkylene glycols, preferably with a molecular weight from 200 to 1000, for example polyethylene glycols, polypropylene glycols and polyethylene-propylene glycols, silicones, aromatic carboxylates (e.g. dialkylphthalates, trimellitates, benzoates, terephthalates) or aliphatic dicarboxylates (e.g. dialkyladipates, sebacates, azelates, citrates and tartrates), fatty acid esters, such as glycerol mono-, glycerol di- or glycerol triacetate or sodium diethylsulphosuccinate. The concentration of plasticizers, if present, is generally 0.5 to 30, preferably 0.5 to 10 wt. %, relative to the total weight of polymer and plasticizers. The amount of plasticizers is advantageously at most 30 wt. %, relative to the total weight of polymer and plasticizers, so that—in the range of solid forms—formulations and dosage forms are produced that are stable in storage and do not display any low-temperature flow.

Sugar alcohols such as sorbitol, xylitol, mannitol, maltitol; or sugar alcohol derivatives such as isomalt or hydrogenated condensed Palatinose as described in DE 102 62 005.

Solubilizers, such as sorbitan fatty acid esters, polyalkoxylated fatty acid esters, such as polyalkoxylated glycerides, polyalkoxylated sorbitan fatty acid esters or fatty acid esters of polyalkylene glycols; or polyalkoxylated ethers of fatty alcohols. A fatty acid chain in these compounds as a rule comprises 8 to 22 carbon atoms. The polyalkylene oxide blocks comprise on average 4 to 50 alkylene oxide units, preferably ethylene oxide units, per molecule.

Suitable sorbitan fatty acid esters are sorbitan monolaurate, sorbitan monopalmitate, sorbitan monostearate, sorbitan monooleate, sorbitan tristearate, sorbitan trioleate, sorbitan monostearate, sorbitan monolaurate or sorbitan monooleate.

Suitable polyalkoxylated sorbitan fatty acid esters are for example polyoxyethylene(20)sorbitan monolaurate, polyoxyethylene(20)sorbitan monopalmitate, polyoxyethylene(20)sorbitan monostearate, polyoxyethylene(20)sorbitan monooleate, polyoxyethylene(20)sorbitan tristearate, polyoxyethylene(20)sorbitan trioleate, polyoxyethylene(4)sorbitan monostearate, polyoxyethylene(4)sorbitan monolaurate or polyoxyethylene(4)sorbitan monooleate.

Suitable polyalkoxylated glycerides are obtained for example by alkoxylation of natural or hydrogenated glycerides or by transesterification of natural or hydrogenated glycerides with polyalkylene glycols. Commercially available examples are polyoxyethyleneglycerol ricinoleate-35, polyoxyethyleneglycerol trihydroxystearate-40 (Cremophor® RH40, BASF AG) and polyalkoxylated glycerides that can be purchased under the trade names Gelucire® and Labrafil® from Gattefosse, e.g. Gelucire® 44/14 (lauroyl-macrogol-32-glyceride, produced by transesterification of hydrogenated palm kernel oil with PEG 1500), Gelucire® 50/13 (stearoyl-macrogol-32-glyceride, produced by transesterification of hydrogenated palm oil with PEG 1500) or Labrafil M1944 CS (oleoyl-macrogol-6-glyceride, produced by transesterification of apricot kernel oil with PEG 300).

A suitable fatty acid ester of polyalkylene glycols is e.g. PEG-660-hydroxystearic acid (polyglycol ester of 12-hydroxystearic acid (70 mol. %) with 30 mol. % ethylene glycol).

Suitable polyalkoxylated ethers of fatty alcohols are e.g. macrogol-6-cetylstearyl ether or macrogol-25-cetylstearyl ether.

Solubilizers are typically added to the powder mixture in an amount from 0.1 to 15 wt. %, preferably 0.5 to 10 wt. %.

Disintegrants, such as crosslinked polyvinylpyrrolidone and crosslinked sodium carboxymethyl cellulose.

Extenders or fillers, such as lactose, cellulose, silicates or silica, Lubricants, such as magnesium stearate and calcium stearate, sodium stearyl fumarate, Colorants, such as azo dyes, organic or inorganic pigments or colorants of natural origin, Stabilizers, such as antioxidants, photostabilizers, hydroperoxide decomposers, radical scavengers, stabilizers against microbial attack.

The mass typically contains
10 to 90 wt. %, preferably 30 to 80 wt. %, of thermoplastic polymer,
0.5 to 80 wt. %, preferably 10 to 60 wt. %, of active substance, and
0 to 40 wt. %, preferably 0 to 30 wt. % of optional excipients.

Advantageously, the components or some of the components of the melt are mixed into a powder mixture prior to heating. Mixing of the components into the powder mixture is carried out in usual mixers, such as plough-share mixers, shaking or tumbling mixers and the like.

The powder mixture is heated in a device that is usually employed for this purpose. Devices that are particularly suitable are heatable extruders or kneaders, such as mixer-kneader reactors (e.g. ORP, CRP, AP, DTB from the company List or Reactotherm from the company Krauss-Maffei or Ko-Kneter from the company Buss), divided trough kneaders (trough mixers) and internal mixers or rotor/stator systems (e.g. Dispax from the company IKA). The residence time of the mass in the extruder is preferably less than 5 minutes, in particular less than 3 minutes.

The extruders that can be used are single-screw machines, intermeshing-screw machines or alternatively multiple-shaft extruders, in particular twin-screw extruders, co-rotating or counter-rotating, and optionally equipped with kneading disks. Co-rotating twin-screw extruders are especially preferred.

Depending on its design, the extruder or kneader is charged continuously or batchwise, in the usual way. The powder mixture is preferably introduced in free feed, e.g. via differential dosing scales.

Use of continuous kneaders or extruders is preferred. The powder mixture of polymer and active substance is fed at an inlet end into an elongated extruder housing; the mixture is heated to obtain a melt; the melt is moved through the extruder housing to an outlet end of the extruder housing; and a sufficient counterpressure is created in the extruder housing so that the melt emerges from an outlet end of the extruder housing as a continuous extrudate.

As a rule, the extruder housing and the screws are divided into segments. The housing and screws can therefore be combined at will into a plasticizing unit with raw material feed, deaerating or degassing. The screw geometry can be adapted to the mass that is to be processed, with suitable selection of the order of the screw, kneading and mixing elements. The segments of the extruder housing can have separate temperature control. Heating can be effected for example with resistance heater bands or with a heating medium circulating in the jacket.

In accordance with the embodiments described precisely in the foregoing, at a point of the extruder housing located towards the outlet end, a nonsolvent, seed crystals of the active substance or a derivatization reagent are fed into the extruder housing. Feed of the nonsolvent, the seed crystals of the active substance or the derivatization reagent is carried out in a suitable manner, so that uniform mixing into the melt is achieved. This can be accomplished by a person skilled in the art, for example by selecting the feed point and the screw geometry.

As a rule, the mass obtained is submitted to forming. A large number of shapes can be produced, depending on the tooling used and the type of forming. For example, when using an extruder, the extrudate can be formed between a belt and a roll, between two belts or between two rolls, as described in EP-A-358 105, or by calendering in a calender with two shaping rolls, see for example EP-A-240 904. Small granules can be obtained for example by extrusion and hot or cold granulation of the extrudate.

The cooled masses can then also be ground to powder and compressed to tablets in the usual manner. It is also possible to use tableting auxiliaries such as colloidal silica, calcium hydrogen phosphate, lactose, microcrystalline cellulose, starch or magnesium stearate.

The invention is illustrated in more detail in the following examples.

EXAMPLE 1

A powder mixture of 30 wt. % fenofibrate and 70 wt. % copovidone (Kollidon VA-64, BASF AG Ludwigshafen, Germany) was processed in a kneader at a temperature of 100° C. to a homogeneous, transparent, honey-like melt. 20 wt. % water was added to the clear, homogeneous melt, and the melt turned cloudy spontaneously. After cooling, needle-like crystals with a length of 20-50 µm were found in the cooled, cloudy melt specimens in the polarizing microscope. Analysis of the melt specimen by DSC confirmed the presence of crystalline active substance.

EXAMPLE 2

Comparative Example

Example 1 was repeated, but without adding any water. The clear melt was still clear after cooling, and no recrystallization was observed. Analysis of the melt specimen by DSC showed that the active substance was entirely in noncrystalline form.

EXAMPLE 3

A powder mixture of 20 wt. % fenofibrate, 5 wt. % Labrafil M 1944 CS (oleyl-macrogol-6-glyceride, from Gattefosse, France) and 75 wt. % Copovidone (Kollidon VA-64, BASF AG Ludwigshafen, Germany) was processed in a kneader at a temperature of 100° C. to a homogeneous, transparent, honey-like melt. 20 wt. % water was added to the clear, homogeneous melt, and the melt turned cloudy spontaneously. After cooling, needle-like crystals with a size of less than 10 µm were found in the cooled, cloudy melt specimens in the polarizing microscope. Analysis of the melt specimen by DSC confirmed the presence of crystalline active substance.

EXAMPLE 4

A powder mixture of 20 wt. % fenofibrate, 5 wt. % Tween 20 (polyoxyethylene-20-sorbitan monolaurate) and 75 wt. % copovidone (Kollidon VA-64, BASF AG Ludwigshafen, Germany) was processed in a kneader at a temperature of 100° C. to a homogeneous, transparent, honey-like melt. 20 wt. % water was added to the clear, homogeneous melt, and the melt turned cloudy spontaneously. After cooling, needle-like crystals with a length of 10-20 µm were found in the cooled, cloudy melt specimens in the polarizing microscope. Analysis of the melt specimen by DSC confirmed the presence of crystalline active substance.

EXAMPLE 5

Atibeprone was used as the active substance. The active substance starting material displayed a melting peak at 123° C. in differential scanning calorimetry (DSC).

A powder mixture of 20 wt. % atibeprone and 80 wt. % hydroxypropylcellulose (Klucel E F, Aqualon, Germany) was extruded in a twin-screw extruder at a temperature of 140° C. A clear, transparent extrudate emerged from the extrusion die, and turned very cloudy in the air while still in the plastic state. No elongated, needle-like crystals were found in the cloudy, cooled extrudate specimens using polarization microscopy.

Analysis by DSC showed that the active substance was in two different crystalline polymorphic forms in the cooled extrudate. In addition to the crystal form with melting point of 127° C. already present in the starting material, a further melting peak of a second crystalline form occurred at 108° C.; the two crystal forms were present in the approximate proportions 1:1.

EXAMPLE 6

Comparative Test

The test was performed as described in Example 5, except that the melt emerging from the extruder was discharged through a narrow slot die, producing a thin film (with thickness of about 0.3 mm) from the molten material. Owing to the very large surface area relative to the mass, the film cooled to room temperature very quickly. There was no clouding of the clear melt through recrystallization of the active substance in the melt as in Example 5; the film remained completely transparent even after the melt had hardened.

EXAMPLE 7

The test was carried out as in Example 6, except that the film emerging from the slot die of the extruder was held for a few minutes at a temperature of 80° C. directly after discharge. The film turned very cloudy, and it remained so even after subsequent cooling to room temperature.

EXAMPLE 8

A clear, homogeneous melt was produced from a homogeneous, clear melt comprising 50 wt. % ibuprofen and 50 wt. % copovidone (Kollidon® VA-64, BASF, Germany) at a temperature of 90° C. This melt was kneaded for a further 2 minutes and then finely-powdered sodium carbonate was added to this melt in portions, with further kneading (molar ratio ibuprofen:sodium carbonate=2:1). Gas was evolved, and the melt turned very cloudy. After all of the sodium carbonate had been added, kneading was carried out for a further 3 minutes at 90° C., and then cooling to room temperature without further kneading. Crystalline sodium ibuprofenate was detected (WAXS) in the cooled melt.

The invention claimed is:

1. A method of producing a dosage form comprising a solid dispersion of a microcrystalline active substance, the method comprising the steps of:
   a) melting a thermoplastic polymer with a glass transition temperature Tg of at least 20° C. and dissolving the active substance homogeneously in the melt, wherein solubility of the active substance in water is less than 5 g/100 mL at 22° C., thereby obtaining a mass;
   b) prior to complete solidification of the mass obtained, initiating controlled crystallization of the active substance in the mass obtained by at least one of:
      adding water,
      adding seed crystals of the active substance,
      adding a derivatization reagent, or
      holding the mass obtained at a temperature of at least 35° C., which temperature is below the temperature at which the active substance is completely soluble in the mass, for a sufficient length of time for initiation of crystallization of the active ingredient to occur; and c) cooling the mass;

thereby obtaining, without grinding of the active substance, crystals of active substance having an average particle size of from 500 nm to 100 µm, wherein the crystals of active substance are embedded in a matrix of the thermoplastic polymer and stabilized against agglomeration.

2. The method as claimed in claim 1, wherein the derivatization reagent is selected from an acid and a base.

3. The method as claimed in claim 1, wherein the mass comprises at least one plasticizer.

4. The method as claimed in claim 1, further comprising:
a) introducing at one inlet end into an elongated extruder housing powder mixture of the thermoplastic polymer and the active substance;
b) heating the mixture in the extruder housing in order to obtain a melt;
c) propelling the melt through the extruder housing to an outlet end of the extruder housing;
d) creating a sufficient counterpressure in the extruder housing, so that the melt is discharged from the outlet end of the extruder housing as a continuous extrudate; and
e) initiating controlled crystallization of the active substance.

5. The method as claimed in claim 4, wherein a nonsolvent, seed crystals of the active substance or a derivatization reagent is fed into the extruder housing at a point of the extruder housing located towards the outlet end, and mixed with the melt.

6. The method of claim 1, wherein the microcrystalline active substance is fenofibrate or paracetamol.

7. The method of claim 1, wherein controlled crystallization of the active substance in the mass obtained is initiated by holding the mass obtained at a temperature of at least 35° C., which temperature is below the temperature at which the active substance is completely soluble in the mass, for a sufficient length of time for initiation of crystallization of the active ingredient to occur.

8. The method as claimed in claim 7, wherein the mass comprises at least one plasticizer.

9. The method as claimed in claim 7, further comprising:
a) introducing at one inlet end into an elongated extruder housing powder mixture of the polymer and the active substance;
b) heating the mixture in the extruder housing in order to obtain a melt;
c) propelling the melt through the extruder housing to an outlet end of the extruder housing;
d) creating a sufficient counterpressure in the extruder housing, so that the melt is discharged from the outlet end of the extruder housing as a continuous extrudate; and
e) initiating controlled crystallization of the active substance.

10. The method of claim 7, wherein the microcrystalline active substance is fenofibrate or paracetamol.

11. The method of claim 1, further comprising grinding the mass obtained from step c) into a powder and compressing the powder to form a tablet.

12. The method of claim 1, wherein the thermoplastic polymer is copovidone.

13. The method of claim 1, wherein the solubility of the active substance in water is less than 1 g/100 mL at 22° C., thereby obtaining a mass.

* * * * *